United States Patent

Johnson

[11] Patent Number: 5,195,981
[45] Date of Patent: Mar. 23, 1993

[54] HOLDER FOR ELONGATED MEMBERS

[76] Inventor: Melissa C. Johnson, 758 Main St., Leominster, Mass. 01453

[21] Appl. No.: 802,620

[22] Filed: Dec. 5, 1991

Related U.S. Application Data

[62] Division of Ser. No. 451,579, Dec. 18, 1989, Pat. No. 5,100,393.

[51] Int. Cl.[5] .............................................. A61M 25/02
[52] U.S. Cl. ............................. 604/180; 128/DIG. 26; 604/174
[58] Field of Search .................. 604/179, 180, 174; 128/DIG. 26; 29/302, 306

[56] References Cited

U.S. PATENT DOCUMENTS

| | | | |
|---|---|---|---|
| 774,143 | 11/1904 | Adams | 24/302 |
| 2,974,916 | 3/1961 | Richey | 24/302 |
| 3,387,341 | 6/1968 | Mates et al. | 24/306 |
| 3,826,254 | 7/1974 | Mellor | 604/180 |
| 3,834,380 | 9/1974 | Boyd | 604/180 |
| 3,946,742 | 3/1976 | Eross | 128/DIG. 26 |
| 3,994,048 | 11/1976 | Rosenthal | 24/308 |
| 4,025,015 | 5/1977 | Kolic | 128/DIG. 26 |
| 4,047,651 | 9/1977 | McMullen | 24/306 |
| 4,220,302 | 9/1980 | Hampton et al. | 24/306 |
| 4,333,463 | 6/1982 | Grist | 604/180 |
| 4,392,857 | 7/1983 | Beran | 604/179 |
| 4,639,980 | 2/1987 | Peterson | 24/302 |
| 4,700,432 | 10/1987 | Fennell | 604/179 |
| 4,702,736 | 10/1987 | Kalt et al. | 128/DIG. 26 |
| 4,822,342 | 4/1989 | Brawner | 604/180 |
| 4,874,380 | 10/1989 | Mesketh | 604/180 |

Primary Examiner—Paul J. Hirsch
Attorney, Agent, or Firm—Lane, Jr. Munson H.

[57] ABSTRACT

A tube holder adapted to be applied to the body to correctly position a tube and comprising a flat base for application to the body, and on the base at the center thereof being a tube holder comprising a length of material riveted to the base and having a connection means on the end portions of the material to make a tie. The rivet may be one piece and permanent or in two pieces and snap fastened and unfastened.

7 Claims, 1 Drawing Sheet

HOLDER FOR ELONGATED MEMBERS

RELATED APPLICATION

This a divisional of my copending application Ser. No. 07/451,579 filed on Dec. 18, 1989 U.S. Pat. No. 5,100,393.

BACKGROUND OF THE INVENTION

This invention is directed in general but not limited to medical tube holders, e.g. catheter holders as exemplified in U.S. Pat.No. 4,165,748. The present invention presents improvements thereon, and improvements over the other known prior art. Some good ideas in this area turn out to be too expensive, especially for disposable use as practiced in hospitals, etc.; also some tube holders are not sufficiently versatile and cannot be conveniently used for gastrectomy tubing, prostatectomy usage, dialysis, and leg bags, and the like. This invention is intended to provide a disposable, versatile, and economic holder that is safe for any use similar to catheters, and also in other relations.

SUMMARY OF THE DISCLOSURE

A flat, semi-flexible base sheet adapted for pressure-sensitive adhesion to the human body and elsewhere holds at its center a strip of flexible material which will form a loop to encircle the tube, rod, or the like that is to be temporarily but positively secured to the body in desired position, with the tube or rod lying across the base sheet in parallelism thereto. Then, if desired, the tube, rod, or other member wrapped about with the loop, can be ripped off the base sheet, to be free thereof; or the loop can be secured to the base in the first place as a two part snap-fastener of conventional type, and thus the loop can be snapped off the base, and then if conditions require, it can be re-secured to the base sheet. Also, when the loop is snapped fastened to the base sheet, the loop is capable of 360 degree rotation, while still being held to the base sheet, on an axis at right angles to the base sheet, and the loop, for precise positioning.

Many variations of the concept exist. The retaining loop may be any size and shape. It may be a short piece of flexible cloth or tape with hook and loop fasteners to hold the member therein, but it may also be semi-rigid, e.g. plastic trough into which the member to be held is snapped, or it could be a closed clasping element wherein once the member to be held is attached, it cannot become separated without being cut away. Instead of a two part snap fastener to rotatively secure the loop to the base, a simple rivet could be used, and the loop would then be permanently and non-rotatively secured to the base.

PREFERRED EMBODIMENTS OF THE INVENTION

Figure 1:
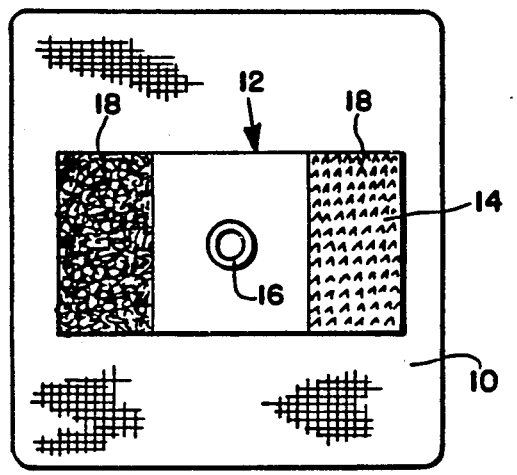
FIG. 1 is a plan view of one form of the invention ready for use.

FIG. 1 illustrates one of the forms of the invention which basically comprises a flat, flexible, base sheet 10 that preferably has one surface with pressure-sensitive material and protective but removable cover to apply the base sheet 10 to any surface for securement thereto, as fully shown in U.S. Pat. No. 4,165,748, and as generally known in the art. This base sheet 10 has at its opposite surface a holder 12 to hold the tube or rod, etc. Thus the base sheet 10 is applied, e.g. to the body of a patient by the adhesive, and the tube, etc., secured thereto by holder 12.

Figure 3:
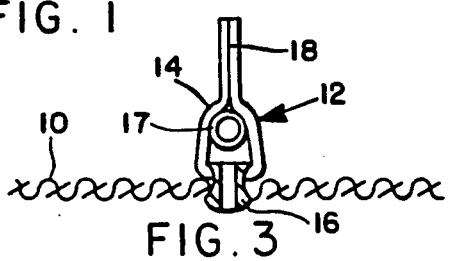
FIG. 3 is an edge view of the holder of FIG. 1 shown in useful position.

In all cases in this invention, wherein the holder may vary widely per se, the holder is secured to the base sheet by either one of two different fasteners, the fasteners themselves being well-known, i.e., a fixed rivet or a swivel snap fastener such as is used on garments in place of buttons. The disclosure shows various actual holders that may be used as part of the entire device. In FIG. 1, for example, a flexible fabric strip 14 is centrally secured to the base sheet by a rivet 16, and this means that strip 14 cannot be removed from the base sheet as the rivet clasps both base sheet 10 and strip 14 firmly together. The strip 14, however, may be bent up, as in FIG. 3, to clasp the tube 17, the ends of the strip 14 being applied with facing areas 18 spaced from the rivet 16, that are provided with pressure sensitive adhesives or hook and hoop structure.

Figure 2:
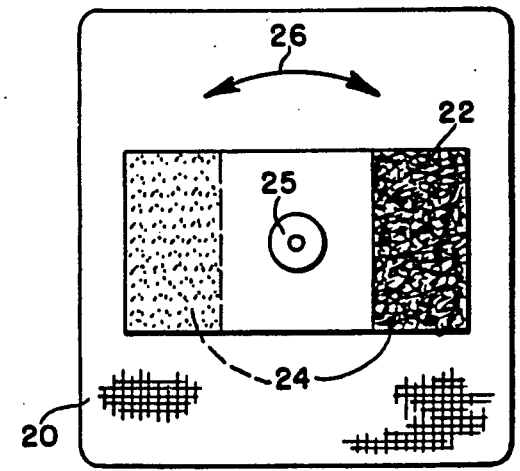
FIG. 2 is a like view of a modification.
Figure 4:
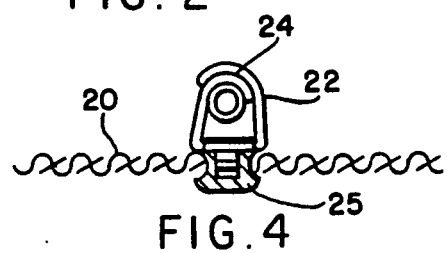
FIG. 4 is an edge view of the holder of FIG. 2 shown in useful position.

The embodiment of FIGS. 2 and 4 is very similar, the base sheet 20 being the same as in FIG. 1, and the tube holding strip 22 may be the same, but as a variation the strip areas 24 that bear adhesive or hook and loop construction are not facing but at opposite sides of the strip so that the tube is held by overlapping the ends of the strip. The main difference is that the fastener of holder strip 22 to the base sheet 20 is a two part swivel snap fastener 25 that can be snapped onto the base sheet, rotated as desired, and snapped apart if wanted. The arrow 26 indicates the swivel action, that is on an axis at right angles to the base sheet 20 and the tube, etc., held therein.

Figure 5:
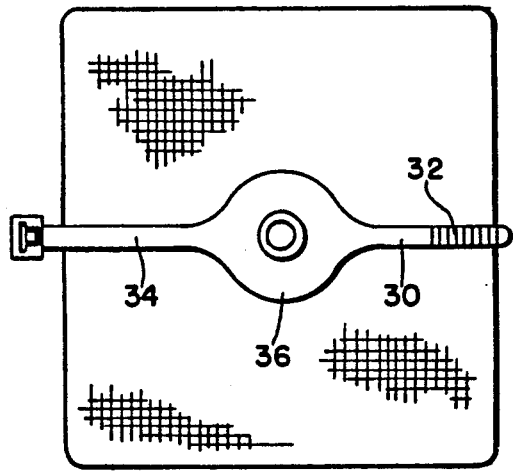
FIG. 5 is a plan view with another modification.
Figure 6:
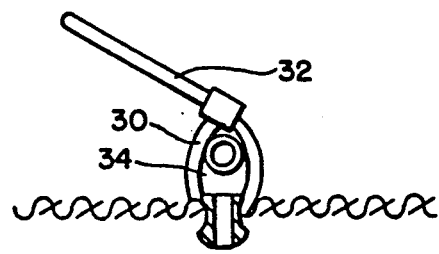
FIG. 6 is an edge view of FIG. 5 shown in use.

FIGS. 5 and 6 illustrate an irreversible fastener 30, that are well-known, as shown by the GB ties made by Gardner-Bender, Inc., of Milwaukee. These are of semi-rigid plastic with a notched end 32 to enter an opening in end 34 and become fastened. A point of novelty here, however, is the central enlargement 36 by which to fasten the entire tube holding fastener by a central rivet or selectively by a two part snap fastener as in FIG. 2.

Figure 7:
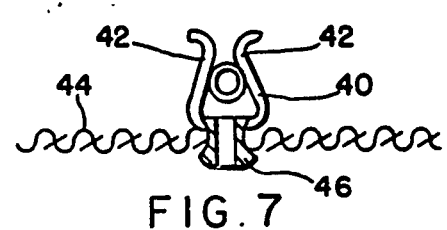
FIG. 7 is an edge view of a still further modification.

While there may be many other tube holders, another efficient one is the U-shaped snap 40 of FIG. 7. Here, the tube is merely pushed down between two resilient arms 42 of predetermined spacing, the bottom of the U being held to the base sheet 44 by a rivet or snap 46.

Such a rivet is usually of one piece and once crimped in position is permanent. A snap is of two parts, each crimped to its own piece or support, and may be snapped together and apart many times. These articles are old and well-known per se.

I claim:

1. A holder for tubes, rods or other elongated members comprising:

a flat, flexible support base having opposite surfaces, a member holder means mounted on one surface of said base for holding a tube, rod or other elongated member on said base, a rivet connecting said member holder means to said base, said rivet being permanently crimped to said base and to said member holder means so that the base and member holder means are permanently secured, said flat flexible support base comprising a thin sheet of flexible material which is conformable to a separate flat or contoured surface, a layer of pressure sensitive adhesive means covering the surface of said sheet opposite the surface on which said member holder means is mounted for removably securing said base to a separate supporting surface, a removable protective cover covering said pressure sensitive adhesive means, said member holder means comprising a strip of flexible material having opposite end portions bendable over a tube, rod or other elongated member placed on said strip between the ends thereof, conjoining means on said opposite end portions of said strip for releasably securing said end portions together about a tube, rod or other elongated member which is placed on said strip between said end portions, said rivet extending through said flat, flexible support base and said strip of flexible material intermediate the end portions of said strip.

2. The holder of claim 1 wherein said conjoining means comprises hook and loop fasteners.

3. The holder of claim 1 wherein said conjoining means comprises pressure sensitive adhesive.

4. The holder of claim 1 wherein said conjoining means comprises notches on one of said end portions and an opening in the other of said end portions to receive said one end portion and to secure said end portions in a loop about a tube, rod or other elongated means.

5. The holder of claim 4 wherein said strip of flexible material includes a central enlargement intermediate the end portions of said strip, and said rivet connecting the member holder means to said base extends through the approximate center of said central enlargement, said central enlargement having a width substantially greater then the width of the end portions of said strip.

6. The holder of claim 5 wherein said strip is made of a semi-rigid plastic material.

7. The holder of claim 5 wherein said central enlargement is of a substantially circular configuration.

* * * * *